United States Patent [19]

Farncomb et al.

[11] 4,192,819

[45] Mar. 11, 1980

[54] METHOD FOR PRODUCING HYDRAZINES BY REACTING CHLORAMINE WITH AMMONIA OR AMINES

[75] Inventors: Robert E. Farncomb, Accokeek; Kurt F. Mueller, Oxon Hill; Kerry L. Wagaman, Clinton, all of Md.

[73] Assignee: The United States of America as represented by the Secretary of the Navy, Washington, D.C.

[21] Appl. No.: 934,782

[22] Filed: Aug. 18, 1978

[51] Int. Cl.$^2$ .................... C07C 85/26; C07C 109/02; C07C 109/04
[52] U.S. Cl. ................... 260/583 N; 260/569; 260/583 B; 260/705
[58] Field of Search ............... 260/583 B, 583 N, 569, 260/705

[56] References Cited

U.S. PATENT DOCUMENTS

| | | | |
|---|---|---|---|
| 2,806,851 | 9/1957 | Sisler et al. | 260/569 X |
| 2,876,173 | 3/1959 | Nicolaisen | 260/583 B X |
| 3,098,017 | 7/1963 | Walter et al. | 260/583 B X |
| 3,151,163 | 9/1964 | Nussbaum | 260/583 N |
| 3,168,568 | 2/1965 | Clark et al. | 260/583 B |
| 3,254,952 | 6/1966 | Raleigh et al. | 260/583 B X |
| 4,124,452 | 11/1978 | Henderson | 260/583 B X |

FOREIGN PATENT DOCUMENTS

| | | | |
|---|---|---|---|
| 582143 | 8/1959 | Belgium | 260/583 B |
| 624393 | 7/1961 | Canada | 260/583 B |
| 1274393 | 9/1961 | France | 260/583 B |

*Primary Examiner*—John Doll

[57] ABSTRACT

Monomethylhydrazine and dimethylhydrazine are prepared in a multi-step process which comprises the steps of reacting chlorine and ammonia to form gaseous chloramine, introducing the chloramine into the lower reaction layer of a liquid two-phase caustic-amine or caustic/ammonia system, reacting the chloramine with the available ammonia or the available amine, and then transferring the forming hydrazine from the lower reaction layer to the upper storage layer of the two-phase system.

16 Claims, No Drawings

METHOD FOR PRODUCING HYDRAZINES BY REACTING CHLORAMINE WITH AMMONIA OR AMINES

BACKGROUND OF THE INVENTION

This invention is directed to a method of producing hydrazines, and more particularly to a method of producing high purity unsymmetrical dimethylhydrazine.

UDMH is employed primarily as a fuel for liquid propellant rockets and only relatively small amounts are used industrially for the preparation of agricultural chemicals. As a rocket fuel, UDMH is usually not used neat, but in mixtures containing other hydrazines or amines. These mixtures yield liquid propellants and explosives having proper ballistic, chemical, and physical properties. Some examples are: Aerozine 50, 50% UDMH and 50% hydrazine; MAF-1, 39% UDMH, 50% diethylenetriamine, 10% Acetonitrile, and 1% water; MAF-3, 20% UDMH and 80% diethylenetriamine, and MAF-4, 60% UDMH and 40% diethylenetriamine.

The above illustrates that UDMH is a material which is of great strategic importance to the Defense Department. It is constantly being used and it is imperative that a certain stock-pile is maintained. The average annual consumption of UDMH is in the million pound range. UDMH was prepared in the past on a commercial scale by two different processes, the aqueous Raschig Process and the Nitrosamine Process.

The Raschig Process is outlined below:

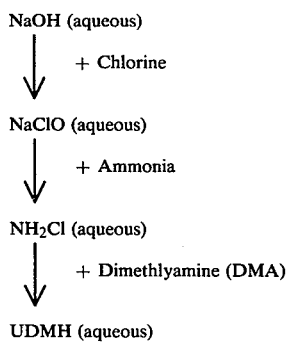

The main problem with this process is that the UDMH has to be isolated from dilute aqueous solution (1–3%) which is a complicated energy consuming operation. UDMH cannot economically be distilled from water as long as its concentration is below approximately 15%, because there is only a minor difference in the compositions of the liquid and the gas phase. To achieve a separation, large quantities of a base such as sodium hydroxide have to be added to the liquid phase and/or the distillation has to be carried out under pressure.

The Nitrosamine Process is outlined below:

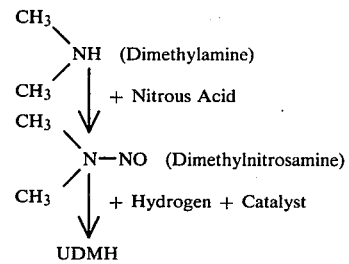

This process has the advantage of producing relatively highly concentrated (15–25%) solutions of UDMH in water which makes the isolation easier and less costly. The entire process in general is more cost effective than the Raschig method. A serious disadvantage of the Nitrosco Process is that the dimethylnitrosamine intermediate is known to be a strong carcinogenic material. The severity of this problem is illustrated by the fact that a large capacity commercial UDMH plant, based on this process, was shut down because of health hazard considerations.

Work described in the literature indicated that UDMH could also be prepared by a modified Raschig Process. It consists of reacting chlorine and an excess of ammonia in the gas phase to chloroamine and then introducing it into liquid dimethylamine (DMA) to form UDMH:

$$2NH_3 + Cl_2 \rightarrow NH_2Cl + NH_4Cl$$

$$NH_2Cl + DMA \rightarrow UDMH + HCl$$

The main problem encountered in trying to scale-up this process was that in conjunction with UDMH a relatively high amount (5–20%) of the formaldehyde hydrazone of UDMH, a side product, was formed. Because of the similarity in the boiling points of the side product and UDMH, it is extremely difficult to effectively separate the two materials by distillation. Since the military specification for the rocket fuel calls for a minimum content of 98% UDMH, any material prepared in the above mentioned fashion is useless. Purification methods other than distillation were found to remove the side product; however, for large scale production they were judged not feasible for economic reasons.

The prior art, included herein by reference, and defined in "Reaction of Chloramine with Anhydrous Primary and Secondary Amines," by G. M. Omietanski, A. D. Kelmers, R. W. Shellmann, and H. H. Sisler, J.A.C.S. 78,3847 (1956) and in U.S. Pat. No. 2,806,851, do not differentiate between UDMH and its formaldehyde hydrazone contaminant. The reason for this is that these test results were analyzed by oxidation with Potassium Iodate, and this system is unable to make that distinction.

SUMMARY OF THE INVENTION

Accordingly, the present invention discloses and claims a method for producing high purity hydrazines which comprises the steps of generating chloramine, reacting the chloramine with either ammonia or an appropriate amine, and isolating and purifying the hydrazine. This process is improved by combining the chloramine reactant with either the ammonia or the appropriate amine reactant so as to reduce the possibility of the free chloramine contacting and reacting with the hydrazine as it is formed. To accomplish this a liquid two-phase system having an upper storage layer and a lower reaction layer is prepared. The upper storage layer comprises either ammonia or a preselected appropriate amine. The lower reaction layer comprises an aqueous caustic solution having a concentration which ranges from more than zero weight percent caustic up to saturated and has dissolved therein enough of the foresaid ammonia or preselected amine to bring the lower reaction layer to equilibrium saturation. Chloramine is then introduced into the lower reaction layer where it contacts and reacts with the available ammonia or the available amine to form the desired hydrazine. Since the hydrazine has a lower density and is relatively insoluble in the caustic phase of this two phase system, it migrates to the top of this lower reaction phase and becomes readily absorbed into the storage phase which primarily consists of either the ammonia or the appropriate amine.

OBJECTS OF THE INVENTION

It is therefore an object of the present invention to provide a method for producing high purity hydrazines.

It is a further object of the present invention to provide a method of preparing high purity unsymmetrical dimethyl hydrazine.

It is still another object of the present invention to provide a means for preparing UDMH which is not contaminated by the formaldehyde hydrazone of UDMH.

Still a further object of the present invention is to provide an economical means of preparing UDMH.

Yet a further object of the present invention is to provide a means for preparing high purity UDMH which eliminates the formation of hazardous wastes and by-products.

Other objects and many of the attendant advantages of this invention will be readily appreciated as the same becomes better understood by reference to the following detailed description.

DESCRIPTION OF THE PREFERRED EMBODIMENTS

In accordance with the present invention there is provided a new three step process for producing hydrazines. First, gaseous chloramine is prepared by reacting chlorine gas with ammonia in the presence of an inert diluent such as nitrogen. Although any chloramine producing system will work, one efficient method of producing the chloramine is by feeding the reactants through two concentric nozzles with chlorine and nitrogen going through the inner portion and ammonia going through the outer portion. The entire nozzle is heated electrically to about 320° to about 350° C. The $NH_3/Cl_2/N_2$ optimum molar feed ratio is about 16/1/1 moles per hour. One such chloramine reactor included herein by reference is described in U.S. Pat. No. 4,038,372 to Mr. Albert J. Colli.

The second step in this three step process is the reaction of the newly formed chloramine with the ammonia or an appropriate amine. The reaction of the chloramine with either the ammonia or the appropriate amine to form the desired hydrazine proceeds at an exceptionally fast rate even at low temperatures. However, the undesireable side reaction wherein the chloramine attacks and reacts with the newly formed hydrazine proceeds at an even faster rate thus generating highly undesirable side products. To minimize the production of these side products it has been found that specific reaction conditions must be observed. The preparation of the reaction media is of primary importance. Depending upon the hydrazine desired, an amine such as a primary, secondary, or tertiary amine, or an ammonia solution is selected. The preferred amines are dimethylamine or monomethylamine. The amine can either be used neat or can be dissolved in any number of organic solvents such as non-reactive aromatic or aliphatic hydrocarbon solvents. To the amine or ammonia solution one must add an aqueous caustic solution such as aqueous sodium hydroxide, aqueous potassium hydroxide, or aqueous lime. The concentration of these solutions should be from more than zero weight percent up to saturated. However, the preferred range is from about 15 to about 70 weight percent, and the most preferred range is from about 20 to about 30 weight percent. Upon the addition of this caustic to the amine or ammonia, there is generated a two-phase system wherein the top storage layer of the system is primarily the amine or the ammonia solution and the bottom reaction layer of the system is primarily the aqueous caustic solution with some of the amine or ammonia dissolved in it. In that the amine is partially soluble in the caustic, the lower reaction layer of the two-phase system rapidly reaches an equilibrium saturation. Once the equilibrium saturation is reached the reaction media is ready for use.

Chloramine is now introduced into the lower reaction layer of the two-phase system. The chloramine can either be in gaseous form or it can be dissolved in an aromatic hydrocarbon solvent such as xylene, or toluene, or in an aliphatic hydrocarbon such as pentane, heptane, or hexane, or in ethers such as diethyl ether. Upon introduction, the chloramine reacts with the available amine or the available ammonia in the lower reaction zone. Because of its relative insolubility and the fact that the forming hydrazine is less dense than the caustic layer, the forming hydrazine rapidly rises to the top of the lower reaction layer of the two-phase system. There, because of its miscibility with the amine or ammonia solution the forming hydrazine is readily absorbed into the upper storage layer. As the amine or the ammonia which is in the reaction layer is consumed, additional reactant migrates from the upper storage layer into the lower reaction layer, thereby maintaining a relatively constant equilibrium solution.

To enhance the transfer of the forming hydrazine from the reaction layer into the storage layer, a means for gently agitating the reaction layer and the boundary layer between reaction layer and storage layer can be introduced. Although this agitating means can be placed in the reaction layer it is preferred that it be placed at the boundary between the two layers. By so placing the agitator, agitating means, contact between the two layers is increased in a narrow band. This enhances the transfer of the forming hydrazine from the lower layer into the upper layer and improves both the rate of reaction and the overall reaction parameters.

Table I shows the test results of a number of runs conducted in accordance with the procedures outlined by the present invention.

Table I

ONE-POT REACTIONS WITH NaOH

| Run No. | Reaction Mixture NaOH (g) | H₂O (g) | DMA (g) | Solvent | Rate of Stirring | Temperature (°C) | NH₂Cl Added (moles) | Reaction Time (min) | Percent UDMH Top Layer | Percent UDMH Bottom Layer | Hydrazone (%) | Yield Based On Cl₂ (%) | Comments |
|---|---|---|---|---|---|---|---|---|---|---|---|---|---|
| 36W | 188 | 438 | 350 | 616 g xylene | Slow | 0-5 | 0.5 / 1.0 | 30 / 60 | 4.1 / 2.51 | — / 2.51 | 20 / 35 | — / 74 | 30% caustic solution; evidence of triazenium salt |
| 38W | 182 | 932 | 350 | — | Slow | 0-5 | 0.5 / 1.0 / 1.6 / 2.0 / 1.0 | 30 / 60 / 95 / 120 / 60 | 2.8 / 4.2 / 5.5 / 5.9 / 5.8 | 0.4 / 0.4 / — / — / 0.4 | — / 5 / 10 / 5 / — | 90 / 89 / 84 / 72 / — | 17% caustic solution; one phase after 95 min |
| 39W | 375 | 875 | 350 | — | Fast | 0-5 | | | | | | | 30% caustic solution; present; evidence for triazenium salt |
| 41W | 375 | 875 | 350 | — | Slow | 0-5 | 0.25 / 0.50 / 0.75 / 1.00 | 30 / 60 / 90 / 120 | 2.19 / 2.78 / 7.1 / 6.5 | 0.35 / — / 0.28 / 0.26 | — / — / — / 5 | — / — / — / 95 | 10 g NaOH added after each 45, 65 & 93 min. top layer contained 56% H₂O at end of reaction; NH₂Cl generator operated at 16/0.5/1 = NH₃ Cl₂/N₂ |
| 42W | 375 | 1125 | 350 | — | Fast | 0-5 | 0.25 / 0.50 / 0.75 / 1.00 | 30 / 60 / 90 / 120 | 1.65 / 4.5 / 3.9 / 3.6 | — / — / — / 0.2 | — / — / — / 30 | — / — / — / 39 | 10 g NaOH added after each 30, 60, & 90 min. NH₂Cl generator operated at 16/0.5/1 = NH₃/Cl₂/N₂ |
| 43W | 375 | 875 | 350 | 450 g xylene | Slow | 0-5 | 0.25 / 0.50 / 0.75 / 1.00 | 30 / 60 / 90 / 120 | 0.65 / 4.05 / 2.9 / 1.8 | 0.0 / 0.1 / 0.3 / 0.65 | — / — / — / — | — / — / — / — | Third layer was formed containing 5.6% UDMH at end of the reaction; NH₂Cl generator operated at 16/0.5/1 = NH₃/Cl₂/N₂ |
| 28 | 120 | 0 | 350 | 480 mls n-PrOH | Slow | −15 | 0.33 | 20 | 2.4 | | 10 | 88 | |
| 6 | 450 | 1050 | 280 g MMA | 450 g ether | Fast | 0-5 | 1 | 60 | 14 MMH | 3 MMH | — | 95 | MMA = monomethylamine; MMH = monomethylhydrazine |

¹Analyzed after solution warmed up to room temperature.

Thus it is apparent that there is provided by this invention a new process for the production of monomethylhydrazine and dimethylhydrazine. It is to be understood that what is described is merely illustrative of the principles of the invention and that numerous arrangements in accordance with this invention may be devised by one skilled in the art without departing from the spirit and scope thereof.

What is claimed and is desired to be secured by Letters Patent of the United States is:

1. In the method of producing hydrazines by generating chloramine, then reacting the chloramine with a nitrogen-containing compound selected from the group consisting of ammonia, monomethylamine, and dimethylamine, and finally isolating and purifying the hydrazine product, improved means for reacting the chloramine with the nitrogen containing compound comprising:
   (1) preparing a two-phase system of;
      (a) an upper storage layer comprising a solution of the nitrogen-containing compound, and
      (b) a lower reaction layer comprising an aqueous caustic solution having a concentration which ranges from more than zero weight percent caustic up to saturated;
   (2) dissolving the solution of nitrogen-containing compound into said reaction layer until equilibrium saturation is attained;
   (3) introducing chloramine into the lower reaction layer of the two-phase system at a rate such that the chloroamine reacts with the nitrogen-containing compound which is available in the reaction layer so as to form the desired hydrazine before the chloramine can reach the storage layer;
   (4) agitating the two-phase system so as to facilitate the transfer of the hydrazine product from the reaction layer to the storage layer, wherein this agitation is performed simultaneously with step (3), and provided that the agitation is gentle enough that the storage layer is not brought into contact with the chloramine.

2. The method of claim 1 wherein said caustic is selected from the group consisting of sodium hydroxide, potassium hydroxide, and lime.

3. The method of claim 2 wherein said caustic is sodium hydroxide.

4. The method of claim 1 wherein said caustic comprises from about 15 to about 70 weight percent of said reaction layer.

5. The method of claim 4 wherein said caustic comprises from about 20 to about 30 weight percent of said reaction layer.

6. The method of claim 14 wherein said reaction layer comprises a saturated caustic solution.

7. The method of claim 1 wherein said chloramine is introduced into said reaction layer in gaseous form.

8. The method of claim 1 wherein said chloramine is dissolved in a solvent selected from the group consisting of aromatic hydrocarbons, aliphatic hydrocarbons, and ethers, and then introduced into the reaction layer.

9. The method of claim 8 wherein said aromatic hydrocarbons are selcted from the group consisting of xylene, and toluene.

10. The method of claim 8 wherein said aliphatic hydrocarbons as selected from the group consisting of heptane, hexane, and pentane.

11. The method of claim 8 wherein said ether is diethyl ether.

12. The method of claim 1 wherein the reaction layer and the boundary layer between the reaction layer and the storage layer are gently agitated.

13. A method according to claim 12 wherein the boundary layer between the reaction layer and the storage layer is gently agitated.

14. A method according to any one of claims 1 to 13 wherein the nitrogen-containing compound is ammonia.

15. A method according to any one of claims 1 to 13 wherein the nitrogen-containing compound is monomethylamine.

16. A method according to any one of claims 1 to 13 wherein the nitrogen-containing compound is dimethylamine.

* * * * *